(12) United States Patent
Chanduszko

(10) Patent No.: US 9,265,636 B2
(45) Date of Patent: Feb. 23, 2016

(54) TWISTED STENT

(75) Inventor: Andrzej J. Chanduszko, Chandler, AZ (US)

(73) Assignee: C. R. Bard, Inc., Murray Hill, NJ (US)

(*) Notice: Subject to any disclaimer, the term of this patent is extended or adjusted under 35 U.S.C. 154(b) by 1385 days.

(21) Appl. No.: 11/753,909

(22) Filed: May 25, 2007

(65) Prior Publication Data

US 2008/0294267 A1    Nov. 27, 2008

(51) Int. Cl.
| | |
|---|---|
| A61F 2/06 | (2013.01) |
| A61F 2/91 | (2013.01) |
| A61F 2/915 | (2013.01) |
| A61F 2/95 | (2013.01) |
| A61F 2/88 | (2006.01) |

(52) U.S. Cl.
CPC . *A61F 2/91* (2013.01); *A61F 2/915* (2013.01); *A61F 2/95* (2013.01); *A61F 2/88* (2013.01); *A61F 2002/91558* (2013.01); *A61F 2002/9517* (2013.01)

(58) Field of Classification Search
CPC .............. A61F 2/82; A61F 2/86; A61F 2/90; A61F 2/91; A61F 2002/91566; A61F 2230/0017
USPC ...................................... 623/1.15, 1.11, 1.22
See application file for complete search history.

(56) References Cited

U.S. PATENT DOCUMENTS

| | | | |
|---|---|---|---|
| 4,886,062 A | 12/1989 | Wiktor | |
| 5,019,090 A | 5/1991 | Pinchuk | |
| 5,116,365 A | 5/1992 | Hillstead | |
| 5,161,547 A | 11/1992 | Tower | |
| 5,226,913 A | 7/1993 | Pinchuk | |
| 5,549,663 A | 8/1996 | Cottone, Jr. | |
| 5,716,396 A | 2/1998 | Williams, Jr. | |
| 5,810,872 A | 9/1998 | Kanesaka et al. | |
| 5,824,053 A | 10/1998 | Khosravi et al. | |
| 5,913,897 A * | 6/1999 | Corso et al. .................. | 623/1.15 |
| 5,938,697 A | 8/1999 | Killion et al. | |
| 6,042,597 A | 3/2000 | Kveen et al. | |
| 6,083,259 A | 7/2000 | Frantzen | |
| 6,117,165 A | 9/2000 | Becker | |
| 6,136,023 A | 10/2000 | Boyle | |
| 6,156,062 A | 12/2000 | McGuinness | |
| 6,193,747 B1 | 2/2001 | von Oepen | |
| 6,287,333 B1 | 9/2001 | Appling et al. | |
| 6,352,552 B1 | 3/2002 | Levinson et al. | |
| 6,355,059 B1 | 3/2002 | Richter et al. | |
| 6,364,904 B1 | 4/2002 | Smith | |

(Continued)

FOREIGN PATENT DOCUMENTS

EP    0801933 A1    10/1997

OTHER PUBLICATIONS

Oct. 29, 2008 International Search Report in International Application No. PCT/US2008/064728 filed on May 23, 2008.

(Continued)

*Primary Examiner* — Katherine Rodjom
(74) *Attorney, Agent, or Firm* — C.R. Bard Intellectual Property Buchalter Nemer, PLC

(57) ABSTRACT

A stent is disclosed and can include a stent body having a longitudinal axis. The stent body can also have a network of struts that can define a plurality of cells defined between interconnected struts. Each of the plurality of cells includes a major axis that is angled with respect to the longitudinal axis to form a cell angle, β.

26 Claims, 9 Drawing Sheets

(56) References Cited

U.S. PATENT DOCUMENTS

| | | |
|---|---|---|
| 6,423,091 B1 | 7/2002 | Hojeibane |
| 6,425,915 B1 | 7/2002 | Khosravi et al. |
| 6,436,132 B1 | 8/2002 | Patel et al. |
| 6,451,052 B1 | 9/2002 | Burmeister et al. |
| 6,488,702 B1 | 12/2002 | Besselink |
| 6,488,703 B1 | 12/2002 | Kveen et al. |
| 6,491,718 B1 * | 12/2002 | Ahmad .................. 623/1.15 |
| 6,503,270 B1 | 1/2003 | Richter et al. |
| 6,517,570 B1 | 2/2003 | Lau et al. |
| 6,551,351 B2 | 4/2003 | Smith et al. |
| 6,610,086 B1 | 8/2003 | Kock et al. |
| 6,620,201 B1 * | 9/2003 | Nadal et al. .................. 623/23.7 |
| 6,736,844 B1 | 5/2004 | Glatt et al. |
| 6,923,828 B1 | 8/2005 | Wiktor |
| 6,929,709 B2 | 8/2005 | Smith |
| 6,949,120 B2 | 9/2005 | Kveen et al. |
| 7,108,714 B1 | 9/2006 | Becker |
| 2002/0143390 A1 * | 10/2002 | Ishii .......................... 623/1.15 |
| 2002/0156525 A1 | 10/2002 | Smith et al. |
| 2003/0050690 A1 | 3/2003 | Kveen et al. |
| 2003/0149474 A1 | 8/2003 | Becker |
| 2003/0176914 A1 * | 9/2003 | Rabkin et al. ................. 623/1.15 |
| 2004/0024446 A1 | 2/2004 | Smith |
| 2004/0049260 A1 * | 3/2004 | Dong ........................... 623/1.15 |
| 2004/0111147 A1 * | 6/2004 | Rabkin et al. ................. 623/1.15 |
| 2004/0149294 A1 | 8/2004 | Gianchandani et al. |
| 2004/0181277 A1 * | 9/2004 | Furst ............................ 623/1.16 |
| 2005/0149081 A1 | 7/2005 | Ricota et al. |
| 2005/0149111 A1 | 7/2005 | Kanazawa et al. |
| 2005/0149168 A1 | 7/2005 | Gregorich |
| 2005/0149169 A1 | 7/2005 | Wang et al. |
| 2005/0149170 A1 | 7/2005 | Tassel et al. |
| 2005/0154447 A1 | 7/2005 | Goshgarian |
| 2005/0154448 A1 | 7/2005 | Cully et al. |
| 2005/0154449 A1 | 7/2005 | Elmaleh |
| 2005/0159803 A1 | 7/2005 | Lad et al. |
| 2005/0159804 A1 | 7/2005 | Lad et al. |
| 2005/0159805 A1 | 7/2005 | Weber et al. |
| 2005/0159806 A1 | 7/2005 | Shanley |
| 2005/0159807 A1 | 7/2005 | Bales et al. |
| 2005/0163954 A1 | 7/2005 | Shaw |
| 2005/0165469 A1 | 7/2005 | Hogendijk |
| 2005/0165470 A1 | 7/2005 | Weber |
| 2005/0165471 A1 | 7/2005 | Wang et al. |
| 2005/0165472 A1 | 7/2005 | Glocker |
| 2005/0165473 A1 | 7/2005 | Denardo |
| 2005/0171569 A1 | 8/2005 | Girard et al. |
| 2005/0171595 A1 | 8/2005 | Feldman et al. |
| 2005/0171596 A1 | 8/2005 | Furst et al. |
| 2005/0177223 A1 | 8/2005 | Palmaz |
| 2005/0181141 A1 | 8/2005 | Flanagan |
| 2005/0182477 A1 | 8/2005 | White |
| 2005/0182478 A1 | 8/2005 | Holman et al. |
| 2005/0182479 A1 | 8/2005 | Bonsignore et al. |
| 2005/0182480 A1 | 8/2005 | Doran et al. |
| 2005/0182481 A1 | 8/2005 | Schlick et al. |
| 2005/0182482 A1 | 8/2005 | Wang et al. |
| 2005/0187605 A1 | 8/2005 | Greenhalgh et al. |
| 2005/0187606 A1 | 8/2005 | Gregorich |
| 2005/0187607 A1 | 8/2005 | Akhtar et al. |
| 2005/0187608 A1 | 8/2005 | O'Hara |
| 2005/0187609 A1 | 8/2005 | Brar et al. |
| 2005/0216076 A1 | 9/2005 | Kveen et al. |
| 2006/0064154 A1 | 3/2006 | Bales et al. |
| 2006/0064155 A1 | 3/2006 | Bales et al. |
| 2006/0064158 A1 | 3/2006 | Bales et al. |
| 2006/0074480 A1 | 4/2006 | Bales et al. |
| 2006/0079955 A1 | 4/2006 | Brown |
| 2006/0111771 A1 | 5/2006 | Ton et al. |
| 2007/0005126 A1 | 1/2007 | Tischler |
| 2007/0016283 A1 | 1/2007 | Greenhalgh et al. |
| 2007/0162112 A1 * | 7/2007 | Burriesci et al. ............. 623/2.36 |

OTHER PUBLICATIONS

Oct. 29, 2008 Written Opinion of the International Searching Authority in International Application No. PCT/US2008/064728 filed on May 23, 2008.

Dec. 1, 2009 International Preliminary Report on Patentability in International Application No. PCT/US2008/064728 filed on May 23, 2008.

* cited by examiner

TWISTED STENT

FIELD OF THE DISCLOSURE

The present disclosure relates generally to surgical devices. More specifically, the present disclosure relates to stents and stent delivery devices.

BACKGROUND

Vascular stenosis is an abnormal narrowing in a blood vessel. Vascular stenosis can include peripheral artery stenosis, coronary artery stenosis, carotid artery stenosis, and renal artery stenosis. There exist several ways to detect vascular stenosis. For example, a vascular stenosis can be detected using a stethoscope to amplify bruit, i.e., noise, within the blood vessel due to turbulent blood flow through the narrowed blood vessel. Alternatively, one or more imaging methods can be used to detect and locate a vascular stenosis. For example, ultrasound, magnetic resonance imaging, and computed tomography can be used to detect and locate a vascular stenosis.

A common cause of vascular stenosis is atherosclerosis. Atherosclerosis, aka, hardening of the arteries, is a disease that affects the arterial blood vessel. Atherosclerosis is caused by the formation of multiple plaques within the arteries. As plaque builds up within an artery, the diameter of the artery is reduced and results in a stenosis.

Vascular stenosis can be treated using a stent. A stent can be from a shape memory material or a non-shape memory material. A stent made from a non-shape memory material can be installed on a balloon catheter and then, threaded through a patient's cardiovascular system to the stenosis. Once the stent is in place within the stenosis, the balloon catheter can be inflated in order to deform the stent and move the stent to an expanded configuration. Thereafter, the balloon catheter can be deflated and withdrawn from the patient.

A stent made from a shape memory material can be installed on a catheter and a sleeve can be placed over the stent. The catheter and sleeve can be threaded through a patient's cardiovascular system to the stenosis. Once the stent is in place within the stenosis, the sleeve can be removed from the stent. When exposed to the patient's body temperature, the stent automatically can move to an expanded configuration that corresponds to a shape memory configuration.

DETAILED DESCRIPTION OF THE DRAWINGS

A stent is disclosed and can include a stent body having a longitudinal axis. The stent body can also have a network of struts that can define a plurality of cells defined between interconnected struts. Each of the plurality of cells includes a major axis that is angled with respect to the longitudinal axis to form a cell angle, b.

In another embodiment, a stent is disclosed and can include a stent body having a proximal end and distal end. The stent body can also have a longitudinal axis. The stent is configured to collapse radially about the longitudinal axis as the proximal end is rotated with respect to the distal end.

In yet another embodiment, a method of preparing a stent for deployment is disclosed. The stent can have a proximal end and a distal end. The method can include grasping the proximal end of the stent, grasping the distal end of the stent, and rotating the proximal end and the distal end with respect to each other in order to move the stent to a collapsed configuration.

In still another embodiment, a stent delivery tool is disclosed and can include an inner carrier catheter. The inner carrier catheter can include a stent engagement area that can be configured to engage a twisted stent and prevent the twisted stent from rotating relative to the inner carrier catheter.

Description of a Stent Delivery Device

Figure 1:
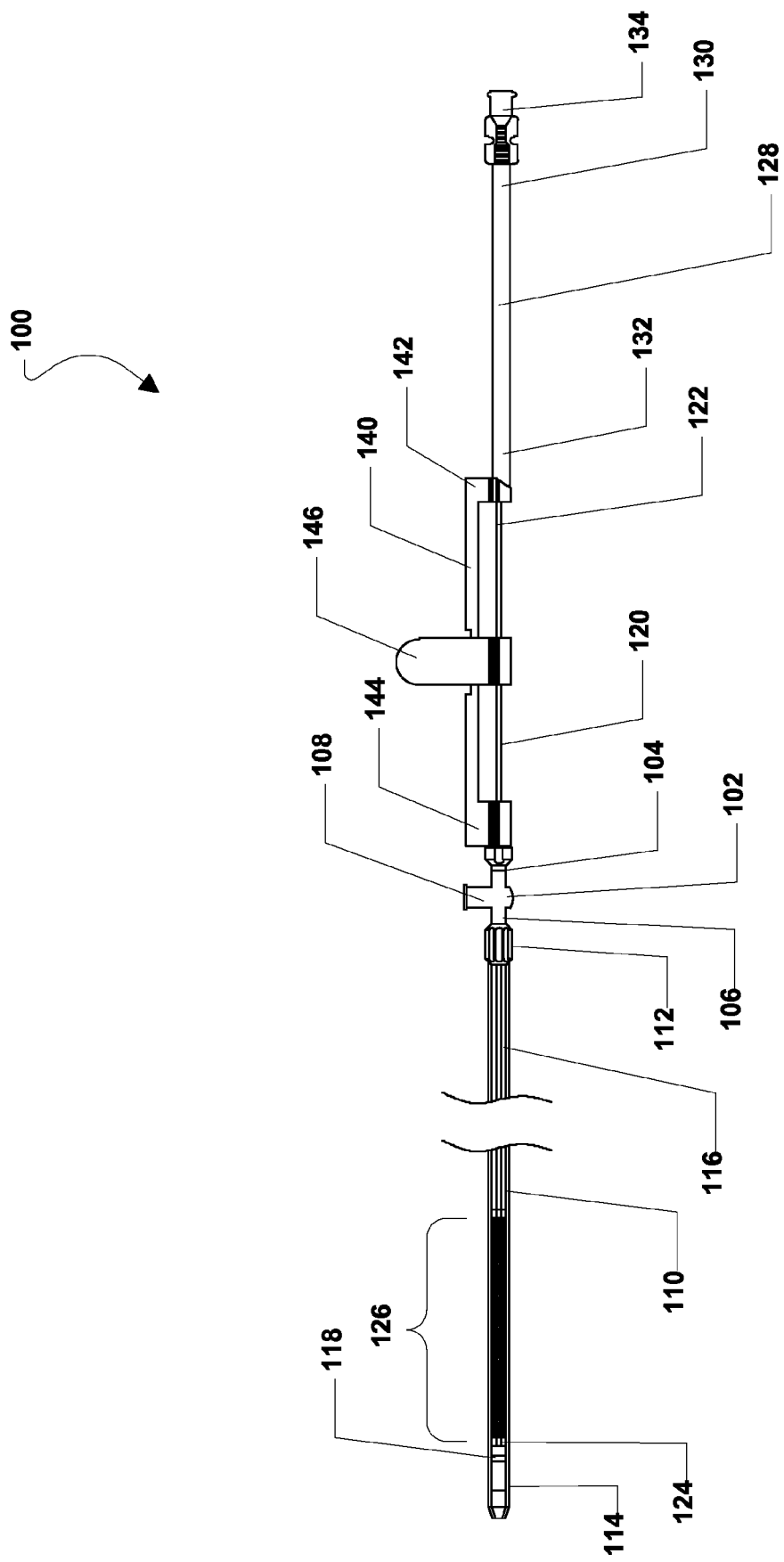
FIG. 1 is a plan view of a stent delivery device.

Referring to FIG. 1, a stent delivery device is shown and is generally designated 100. As shown, the stent delivery device 100 includes a body 102 having a proximal end 104 and a distal end 106. A first syringe attachment 108 can be formed in the body 102 between the proximal end 104 and the distal end 106. In a particular embodiment, the first syringe attachment 108 can be a Luer syringe attachment. The first syringe attachment 108 can provide fluid communication to a lumen formed within an outer sheath 110, described below.

FIG. 1 indicates that the stent delivery device 100 can include an outer sheath 110. The outer sheath 110 can include a proximal end 112 and a distal end 114. Further, the outer sheath 110 can extend from the distal end 106 of the body 102 of the stent delivery device 100. In particular, the proximal end 112 of the outer sheath 110 can be attached to the distal end 106 of the body 102 of the stent delivery device 100. The distal end 114 of the outer sheath 110 can be relatively soft and rounded. The outer sheath 110 can include a lumen 116 formed therein. Further, the distal end 114 of the outer sheath 110 can include a radiopaque band 118.

As illustrated in FIG. 1, the stent delivery device 100 can further include an inner carrier catheter 120. The inner carrier catheter 120 can extend through the body 102 of the stent delivery device 100 and into the lumen 116 formed in the outer sheath 110. The inner carrier catheter 120 can be coaxial with the outer sheath 110. Further, the inner carrier catheter 120 can include a proximal end 122 and a distal end 124. The inner carrier catheter 120 can be formed with a lumen (not shown) that can be sized to fit over a guide wire. In particular, the lumen of the inner carrier catheter 120 can fit over a 0.035 inch guide wire.

As shown in FIG. 1, a stent 126 can be compressed between the inner catheter 120, e.g., the distal end of the inner catheter 120, and the outer sheath 110. A handle 128 can be attached to, or otherwise extend from, the proximal end 122 of the inner carrier catheter 120. The handle 128 can include a proximal end 130 and a distal end 132. The proximal end 130 of the handle 128 can include a second syringe attachment 134. In a particular embodiment, the second syringe attachment 134 can be a Luer syringe attachment. The second syringe attachment 134 can provide fluid communication with the lumen formed within the inner carrier catheter 120.

The stent delivery device 100 can also include a safety clip 140 installed between the body 102 of the stent delivery device 100 and the handle 128 of the inner carrier catheter 120. The safety clip 140 can include a proximal end 142 and a distal end 144. Further, the safety clip 140 can include a butterfly handle 146 between the proximal end 142 of the safety clip 140 and the distal end 144 of the safety clip 140. In a particular embodiment, the stent deliver device 100 can be installed between the body 102 of the stent delivery device 100 and the handle 128 of the inner carrier catheter 120 such that the proximal end 142 of the safety clip 140 abuts the distal end 132 of the handle 128 and the distal end 144 of the safety clip 140 abuts the proximal end 104 of the body 102.

The safety clip 140 can fit over the inner carrier catheter 120. Further, the safety clip 140 can prevent the body 102 of the stent delivery device 100 from moving relative to the handle 128 of the inner carrier catheter 120. Further, the safety clip 140 can prevent the outer sheath 110 from sliding relative to the inner carrier catheter 120. During use, the stent delivery device 100 can be threaded into a cardiovascular system of a patient to a target area. The radio opaque band 118 formed on the outer sheath 110 can be used to guide the stent delivery device into the cardiovascular system of a patient, e.g., with the aid of fluoroscopy. Further, a pair of radiopaque bands on the stent 126 can aid in positioning the stent 126 within the patient. Once the stent 126 is properly positioned, the butterfly handle 146 can be squeezed in order to remove the safety clip 140 from the inner carrier catheter 120 and the stent delivery device 100. Thereafter, the body 102 of the stent delivery device 100 can be moved toward the handle of the inner carrier catheter 120 in order to slide the outer sheath 110 off of the stent 126 and expose the stent 126 inside the patient.

Once the stent 126 is exposed within the patient, the stent 126 can be deployed within the patient by exposing the patient to a laser having a wavelength of approximately seven hundred and eighty nanometers (780 nm). The energy can melt a polymer on the stent 126 and allow the stent 126 to move to a shape memory configuration, e.g., an expanded configuration, within the patient, and be deployed within the patient. After the stent 126 is deployed, the inner carrier catheter 120 can be withdrawn from the patient.

Figure 2:
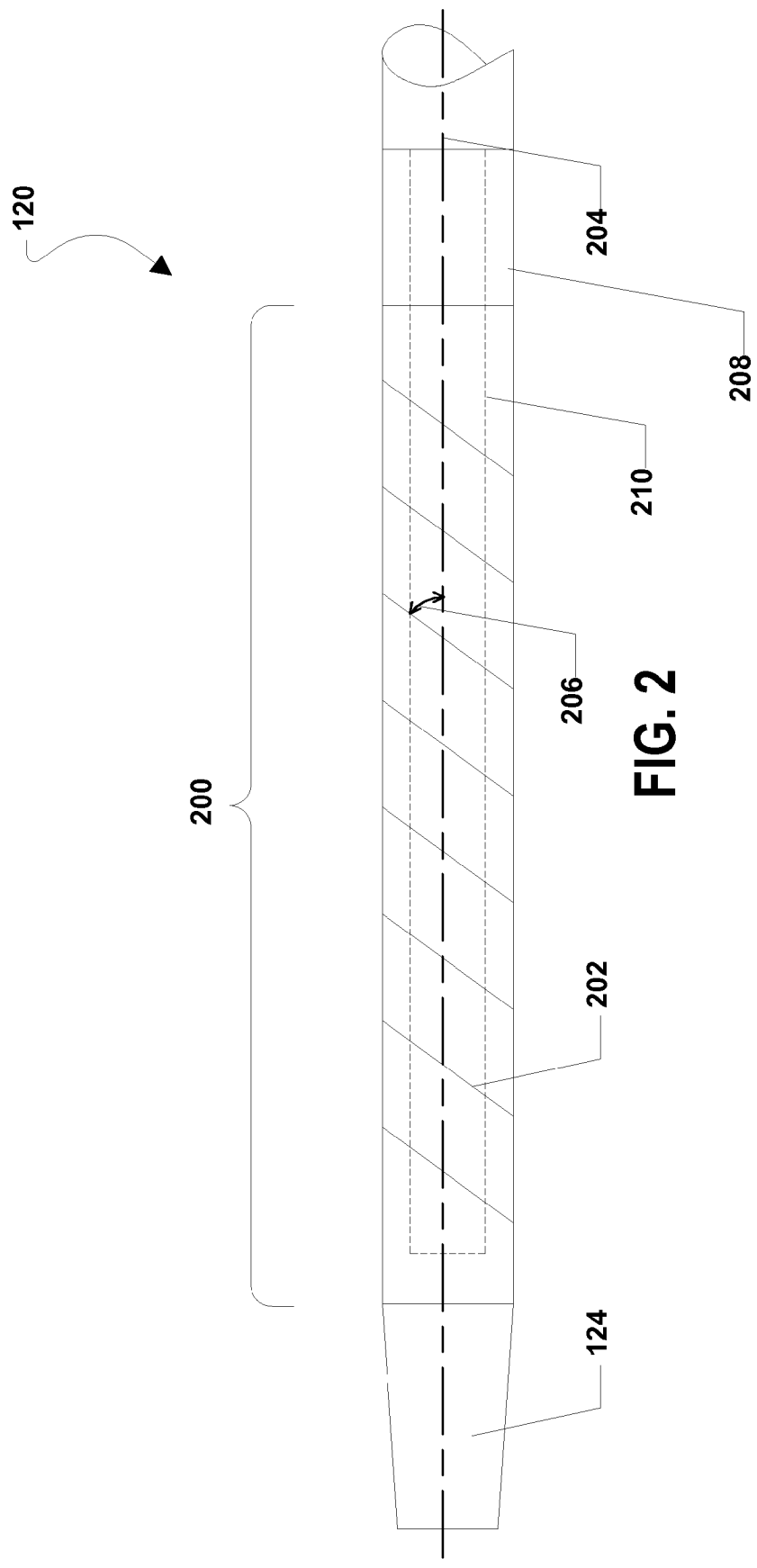
FIG. 2 is a detailed view of a stent delivery device.

FIG. 2 is a detailed view of the inner carrier catheter 120. As shown, the inner carrier catheter 120 can include a stent engagement area 200 near the distal end 124 of the inner carrier catheter 120. As shown, the stent engagement area 200 can include a helical structure 202 extending along the length of the stent engagement area 200. The helical structure 202 can include a helical groove formed in the inner carrier catheter 120. Alternatively, the helical structure 202 can include a raised helical rib, or thread, formed on the inner carrier catheter 120. In a particular embodiment, the helical structure 202 is angled with respect to a longitudinal axis 204 of the inner carrier catheter 120 to form a stent engagement angle 206, $\alpha$.

In a particular embodiment, $\alpha$ can be greater than zero degrees and less than ninety degrees ($0°<\alpha<90°$). In another embodiment, $\alpha$ can be greater than one degree and less than sixty degrees ($1°<\alpha<60°$). In yet another embodiment, $\alpha$ can be greater than two degrees and less than forty-five degrees ($2°<\alpha<45°$). In still another embodiment, $\alpha$ can be greater than five degrees and less than thirty degrees ($5°<\alpha<30°$).

As shown in FIG. 2, the inner carrier catheter 120 can include a tip 208 and the stent engagement area 200 can be formed on the tip of the inner carrier catheter 120. The tip 208 of the inner carrier catheter 120 can be disposed on a post 210 formed on the inner carrier catheter 120. Further, the tip 208 of the inner carrier catheter 120 can rotate on the post 210. Accordingly, when a stent is deployed and the inner carrier catheter 120 is withdrawn from the deployed stent, the tip 208 of the inner carrier catheter 120 can rotate within the deployed stent. The deployed stent can remain stationary within an artery in which the stent is deployed.

Figure 3:
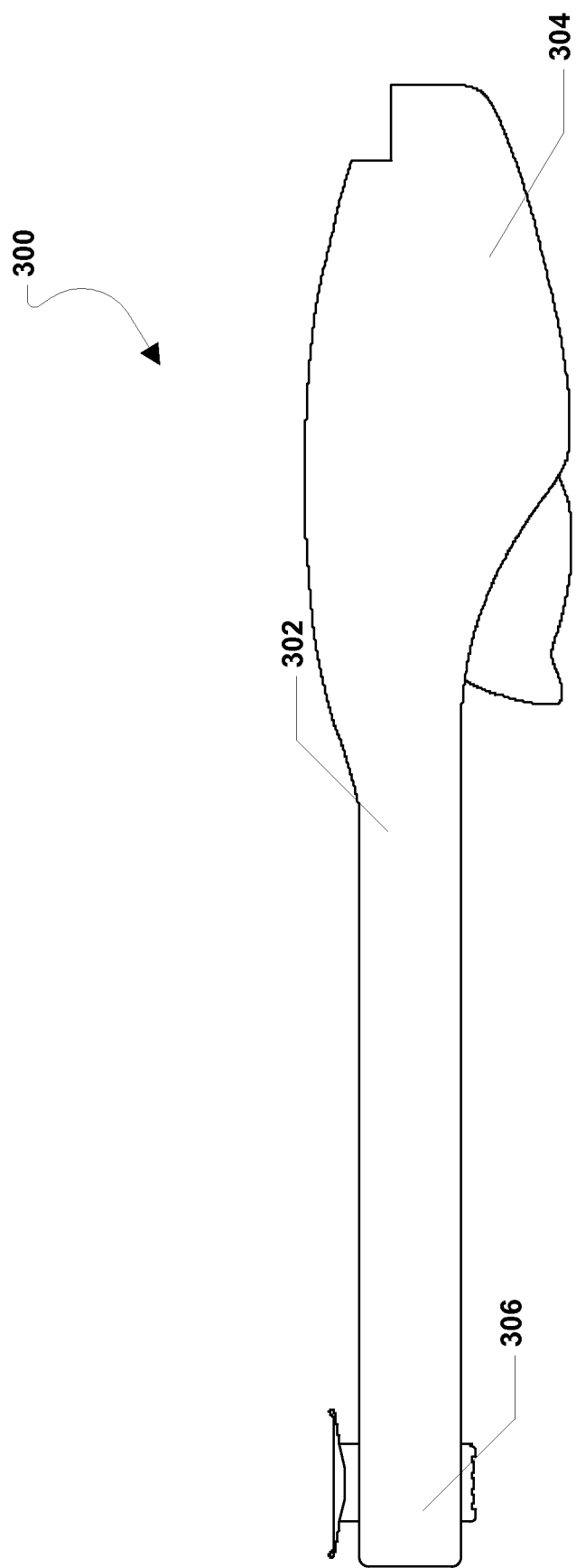
FIG. 3 is a plan view of a handle for a stent delivery device.
Figure 4:
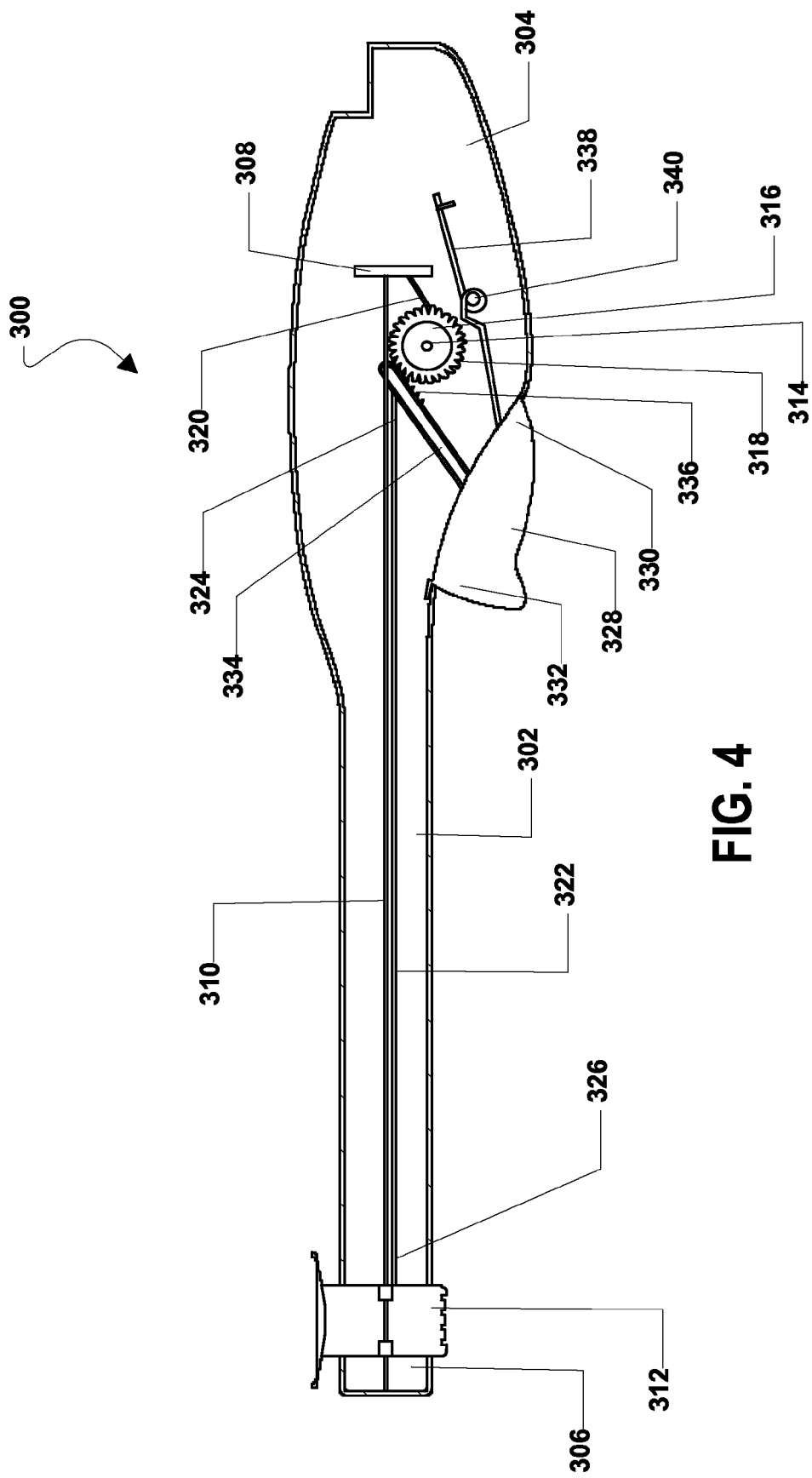
FIG. 4 is a cross-section view of the handle.

FIG. 3 and FIG. 4 illustrate a handle assembly, generally designated 300 that can be used in conjunction with the stent delivery system 100, described above. As shown in FIG. 3 and FIG. 4, the handle assembly 300 can include a housing 302. The housing 302 can be hollow and can include a proximal end 304 and a distal end 306.

As depicted in FIG. 4, a rail support structure 308 can be disposed within the housing 302 near the proximal end 304 of the housing 302. A pair of rails 310 can extend between the distal end 306 of the housing 302 and the rail support structure 308. The handle assembly 300 can also include a carrier 312 that can be slidably disposed on the rails 310. In a particular embodiment, the carrier 312 can be configured to receive the body of a stent delivery system, e.g., the stent delivery system 100, described above.

A shaft 314 can extend from the housing 302 near the rail support structure 308, e.g., between the rail support structure 308 and the distal end 306 of the housing 302. In a particular embodiment, the shaft 314 is substantially perpendicular to the rails 310. A ratchet wheel 316 can be rotatably disposed on the shaft 314. The ratchet wheel 316 can be formed with a plurality of teeth 318 around the outer periphery of the ratchet wheel 316. The handle assembly 300 can also include a pawl 320 extending from the rail support structure 308. The pawl 320 can be configured to engage the ratchet wheel 316, e.g., the teeth 318 of the ratchet wheel 316, and permit rotation of the ratchet wheel 316 in a single direction, e.g., clockwise.

FIG. 4 further shows that the handle assembly 300 can include a cable 322. The cable 322 can include a proximal end 324 and a distal end 326. The cable 322 can extend within the housing along the length of the rails 310. Further, the proximal end 324 of the cable 322 can be wrapped, or otherwise disposed, around the ratchet wheel 316. The distal end 326 of the cable 322 can be attached, or otherwise affixed, to the carrier 312. As the ratchet wheel 316 is rotated, the cable 322 can be rolled onto the ratchet wheel 316 and the carrier 312 can slide along the rails 310 toward the proximal end 304 of the housing 302.

As illustrated in FIG. 4, the handle assembly 300 can also include a trigger 328 extending from the housing 302. The trigger 328 can include a proximal end 330 and a distal end 332. The proximal end 330 of the trigger 328 can be rotatably engaged with the housing 302 and the distal end 332 of the trigger 328 can be free. As such, the trigger 328 can rotate around the proximal end 330 of the trigger 328.

FIG. 4 further indicates that an arm 334 can extend from the trigger 328. The arm 334 can include a plurality of teeth 336 that can engage the teeth 318 formed on the ratchet wheel 316. The handle assembly 300 can also include a spring 338 installed around a post 340 within the housing 302. The spring 338 can bias the trigger 328 outward relative to the housing 302. In a particular embodiment, when the trigger 328 is squeezed inward relative to the housing 302, the arm 334 can rotate the ratchet wheel 316 and cause the carrier 312 to slide within the housing 302 toward the proximal end 304 of the housing 302.

Figure 5:
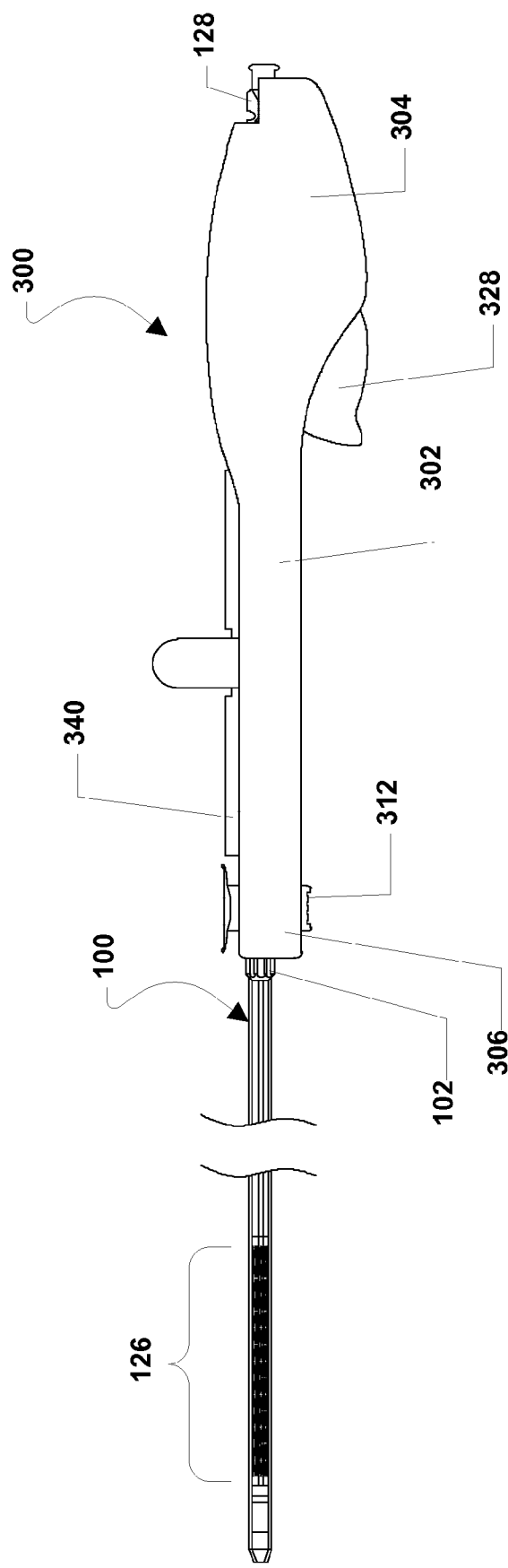
FIG. 5 is a plan view of the stent delivery device engaged with the handle.

In a particular embodiment, the stent delivery device 100 can be engaged with the handle assembly 300 as shown in FIG. 5. Specifically, the body 102 of the stent delivery device 100 can be inserted within the carrier 312. Further, the inner carrier catheter 120 can be installed within the housing 302 of the handle assembly 300 so that the handle 128 of the inner carrier catheter 120 extends through the proximal end 304 of the housing 302. The handle 128 of the inner carrier catheter 120 can be engaged with the housing 302 so that the handle 128 does not move relative to the housing during operation of the handle assembly 300.

Accordingly, the safety clip 140 can be removed from the stent delivery device 100 and the trigger 328 can be squeezed to move the carrier 312 within the handle assembly 300 toward the proximal end 304 of the housing 302. As the carrier 312 moves, the body 102 of the stent delivery device 100 can be moved toward the handle 128 of the inner carrier catheter 120. As the body 102 of the stent delivery device 100 moves toward the handle of the inner carrier catheter 120, the outer sheath 110 can slide off of the stent 126 and expose the stent 126 inside a patient.

Description of a Twisted Stent

Figure 6:
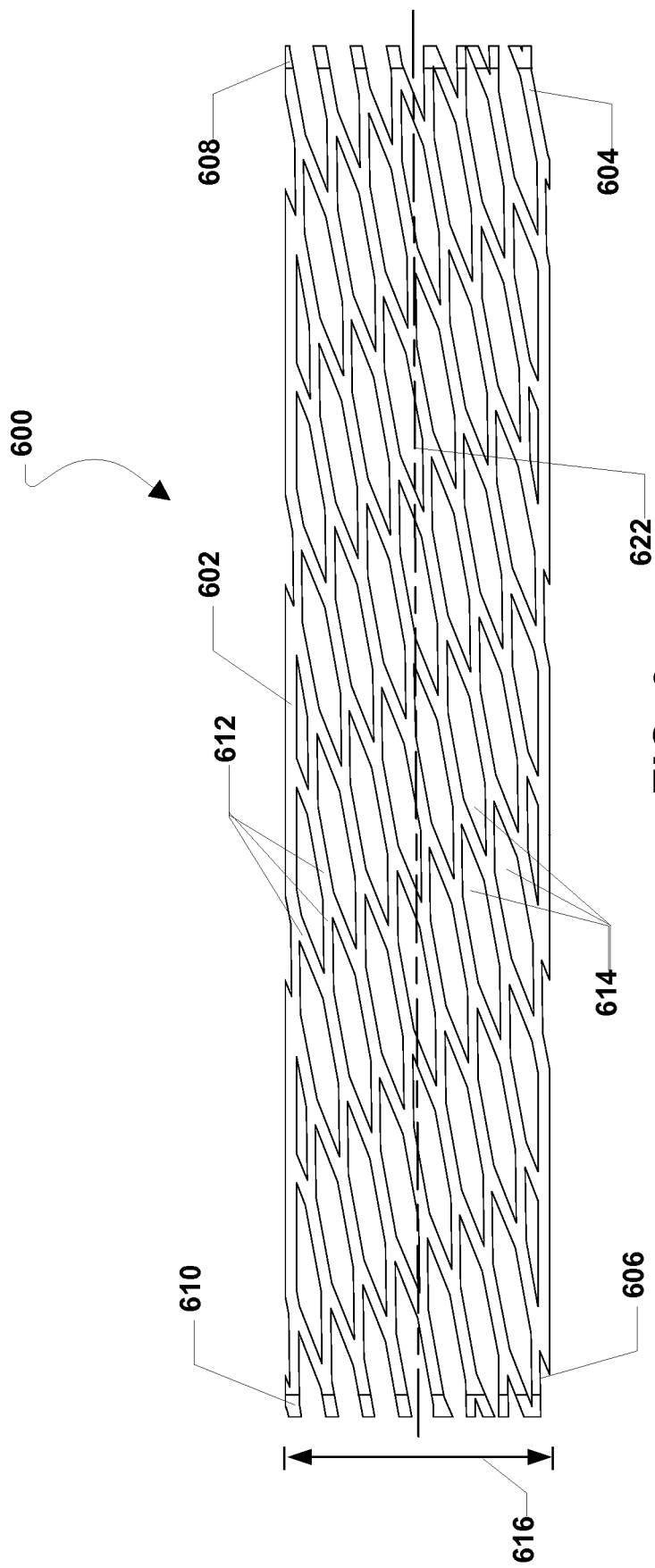
FIG. 6 is a plan view of a stent in a collapsed configuration.
Figure 7:
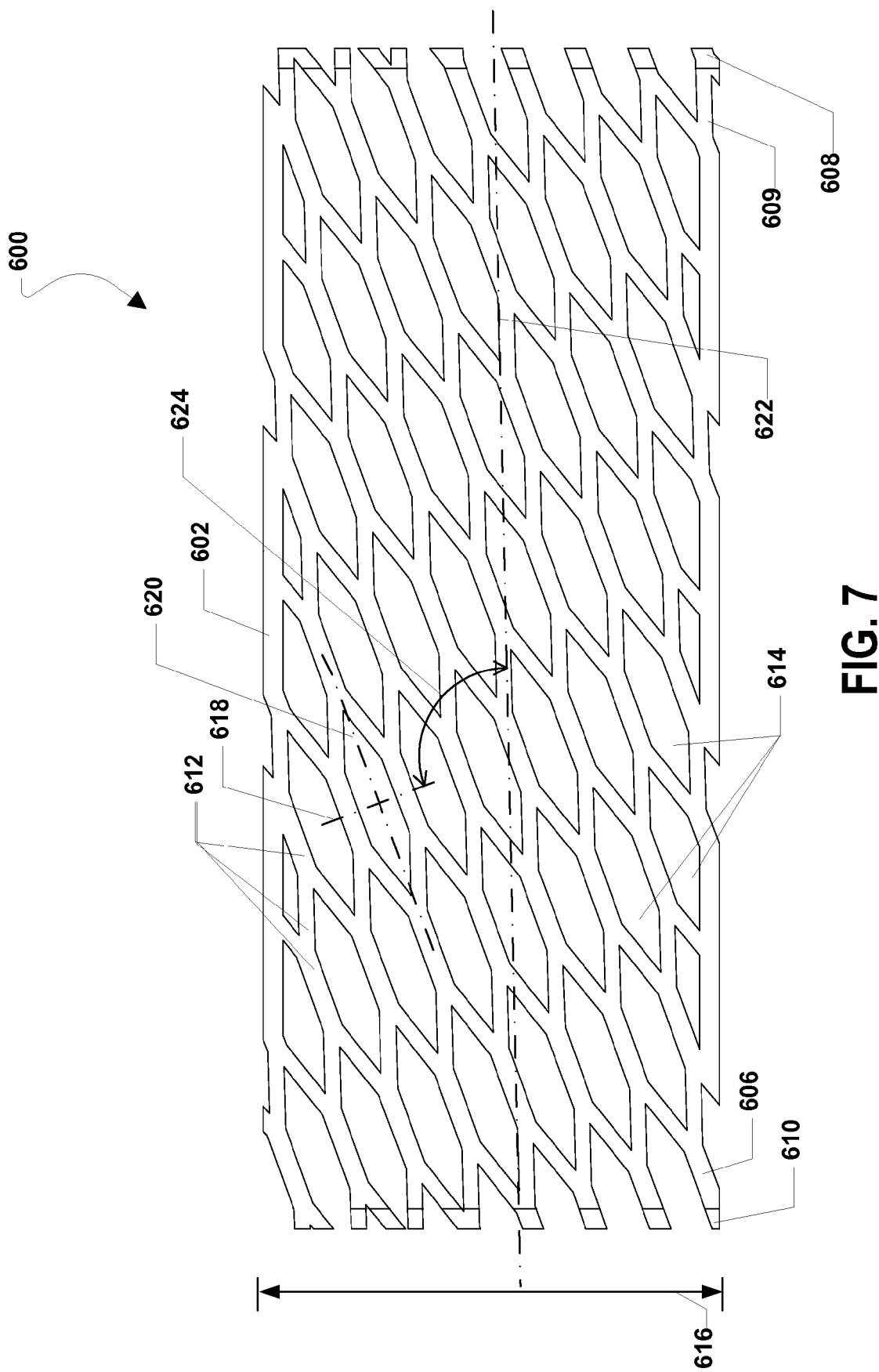
FIG. 7 is a plan view of a stent in an expanded configuration.

Referring to FIG. 6 and FIG. 7, a stent is shown and is generally designated 600. As shown, the stent 600 can include a stent body 602. The stent body 602 can be hollow and generally cylindrical. Further, the stent body 602 can include a proximal end 604 and a distal end 606. The proximal end 604 can include a radiopaque band 608. The distal end 606 can also include a radiopaque band 610.

As indicated in FIG. 6 and FIG. 7, the stent body 602 can include a plurality of struts 612. Further, the struts 612 can establish a plurality of cells 614 within the stent body 602. The struts 612 can be in the form of an interconnected network or matrix that is generally continuous. The struts 612 can form a repeating pattern that can define an array of cells 614. The cells 614, as shown, can be closed. However, it is noted that the stent 600 may have localized areas in which other struts 612 do not form closed cells. In other words, the stent 600 can be a closed-cell stent in which each cell is separate from adjacent cells. Alternatively, the stent 600 can be an open-cell stent in which one or more struts between two or more adjacent cells is removed from the construction of the stent 600.

In a particular embodiment, as shown, each cell 614 can be hexagonally shaped. Alternatively, each cell 614 can be generally diamond shaped, generally elliptical, or another shape that can allow the stent 600 to be collapsed as described herein.

The stent 600 is movable between a collapsed configuration, shown in FIG. 6, and an expanded configuration, shown in FIG. 7. FIG. 6 and FIG. 7 show that the stent 600 can have a diameter 616. The diameter 616 of the stent 600, in the collapsed configuration, is relatively smaller than the diameter 616 of the stent 600 in the expanded configuration. In the collapsed configuration, the cells 614 within the stent body 602 can be collapsed. Further, in the expanded configuration the cells 614 within the stent body 602 can be expanded.

Referring to FIG. 7, the stent 600 can include a longitudinal axis 622. Further, each cell 614 can include a minor axis 618 and a major axis 620. Each cell 614 can include a minor length along the minor axis 618 and a major length along the major axis 620. Moreover, each cell 614 can have an aspect ratio defined by the ratio of the minor length to the major length, when the stent 600 is expanded as shown in FIG. 7. In a particular embodiment, the aspect ratio of each cell 614 can be less than or equal to one (1). In another embodiment, the aspect ratio of each cell 614 can be approximately three-quarters (0.75). In yet another embodiment, the aspect ratio of each cell 614 can be approximately one-half (0.5). In still another embodiment, the aspect ratio of each cell 614 can be approximately one-quarter (0.25).

The major axis 620 of each cell 614 can be angled with respect to the longitudinal axis 622 to establish a cell angle 624, $\beta$. In a particular embodiment, $\beta$ can be greater than zero degrees and less than ninety degrees ($0°<\beta<90°$). In another embodiment, $\beta$ can be greater than one degree and less than sixty degrees ($1°<\beta<60°$). In yet another embodiment, $\beta$ can be greater than two degrees and less than forty-five degrees ($2°<\beta<45°$). In still another embodiment, $\beta$ can be greater than five degrees and less than thirty degrees ($5°<\beta<30°$).

The orientation of the cells 614 can allow the cells to form a helical pattern around the stent body 602 and can allow the stent 600 to be collapsed by grasping the ends of the stent 600 and rotating the ends with respect to each other. This means relative rotation with respect to both ends. For example, the proximal end 604 can be fixed and the distal end 606 can be rotated around the longitudinal axis 622. Further, the distal end 606 can be fixed and the proximal end 604 can be rotated around the longitudinal axis 622. Also, both ends can be rotated in opposite directions relative to each other around the longitudinal axis 622. As the ends of the stent 600 are rotated relative to each other, the cells 614 can collapse. As the cells 614 collapse, the stent 600 can collapse. Further, as the stent 600 collapses, the diameter 616 of the stent 600 can decrease substantially uniformly from an expanded diameter, $D_E$, to a collapsed diameter, $D_C$. In a particular embodiment, a ratio of $D_C$ to $D_E$ is approximately one-half ($D_C/D_E=0.5$). In another embodiment, a ratio of $D_C$ to $D_E$ is approximately one-quarter ($D_C/D_E=0.25$). In yet another embodiment, a ratio of $D_C$ to $D_E$ is approximately one-eighth ($D_C/D_E=0.125$).

In a particular embodiment, the stent 600 can be made from a shape memory material. The shape memory material can include a shape memory polymer, a shape memory metal, or a combination thereof. Further, the shape memory metal can include a metal alloy. The metal alloy can include a nickel titanium alloy, e.g., nitinol. The stent 600 can particularly be made principally from, or even consist essentially of, nitinol.

In an alternative embodiment, the stent 600 can be made from a non-shape memory metal, e.g., stainless steel, titanium, a cobalt-chrome alloy, or a combination thereof. In such a case, the stent 600 can be balloon deployable. In other words, the stent can be installed over a balloon catheter. When the stent is in an appropriate location within a patient, a balloon on the balloon catheter can be inflated in order to expand the stent within the patient.

Figure 8:
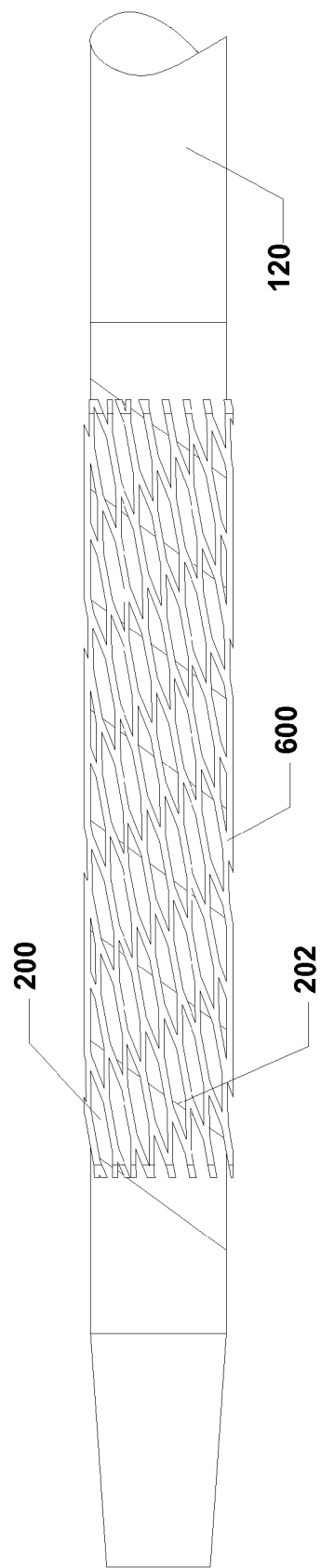
FIG. 8 is a plan view of a stent installed on a stent delivery device.

FIG. 8 illustrates a stent, e.g., the stent 600 described herein, installed on the inner carrier catheter, e.g., the inner carrier catheter 120 described herein. FIG. 8 shows the stent 600 installed over the stent engagement area 200 of the inner carrier catheter 120. As shown, the helical pattern established by the stent cells 614 is arranged so that it is opposite the helical structure 202 within the stent engagement area 200. Accordingly, the helical structure 202 can engage the stent 600 and substantially prevent the stent 600 from rotating on the inner carrier catheter 120 during installation and deployment of the stent.

Description of a Method of Forming a Stent

Figure 9:
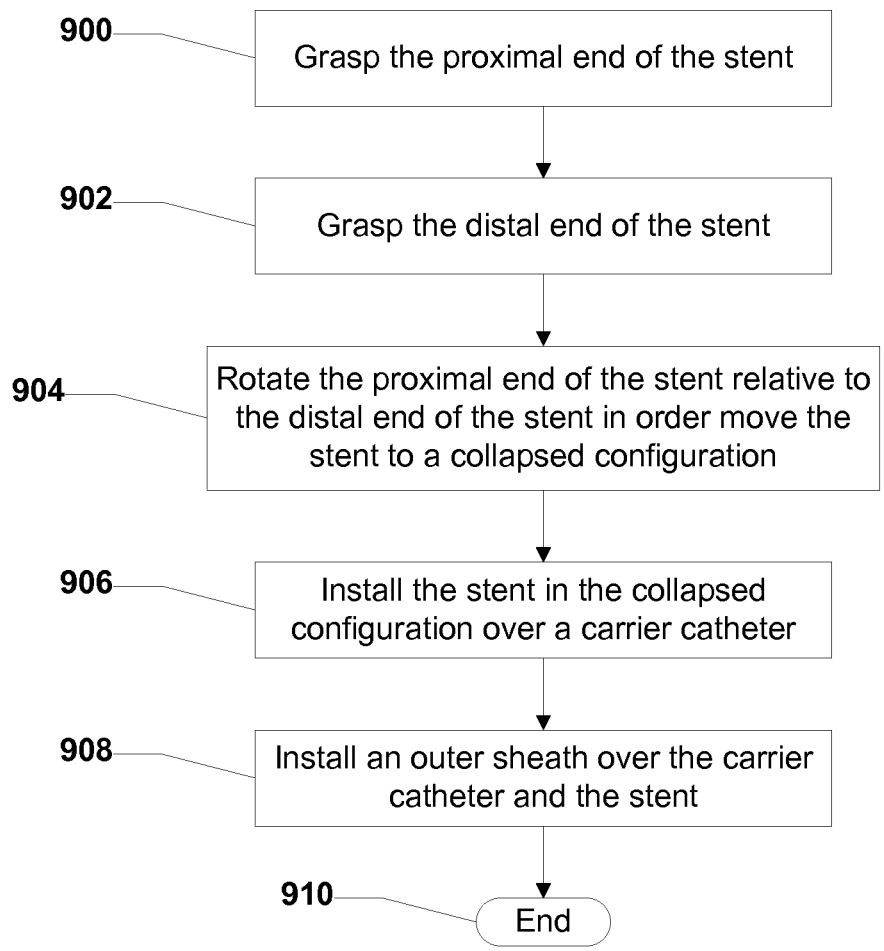
FIG. 9 is a flow chart illustrating one method of installing and deploying a stent.

Referring to FIG. 9, a method of forming a stent is shown and commences at block 900. At block 900, the proximal end of the stent can be grasped. At block 902, the distal end of the stent can be grasped. In a particular embodiment, the ends of the stent can be grasped by a mechanical gripping device. Alternatively, a user can grasp the ends of the stent with his or her fingers.

Moving to block 904, the proximal end of the stent can be rotated relative to the distal end of the stent in order to move the stent to a collapsed configuration. In a particular embodiment, the proximal end of the stent can be rotated in a first direction relative to a longitudinal axis, e.g., clockwise, and the distal end of the stent can be rotated in a second direction relative to the longitudinal axis opposite the first direction, e.g., counterclockwise. In a particular embodiment, the stent can be formed with a plurality of helically arranged cells, as described herein. As the ends of the stent are rotated, the cells can collapse and the stent can collapse.

Continuing to block 906, after the stent is moved to a collapsed configuration, the stent can be installed over a carrier catheter while in the collapsed configuration. Thereafter, at block 908, an outer sheath can be installed over the carrier catheter and the stent. The method can then end at block 910.

In a particular embodiment, a chilling agent, e.g., liquid nitrogen, can be applied to the stent before it is collapsed. Cooling the stent before, or as, the stent is collapsed can aid in collapsing the stent and can substantially prevent the stent from springing outward and expanding when a collapsing force is removed from the stent.

CONCLUSION

With the configuration of embodiments described above, the twisted stent as disclosed herein provides a device that can be used to treat a stenosis. According to an embodiment, the twisted stent includes a stent body having a plurality of cells arranged in a helical pattern around the stent body. The twisted stent can be relatively easily collapsed by grasping the ends of the twisted stent and rotating the ends in opposite directions. As the ends of the stent are rotated, the helical arrangement of the cells allows the cells to collapse. As the cells collapse, the stent collapses. Embodiments not only provide stent configurations that have superior deployment characteristics, but also have reduced profiles.

Accordingly, embodiments can be moved from a collapsed configuration to an expanded configuration and then, returned to a collapsed configuration. For example, a stent can be moved from a collapsed configuration to an expanded configuration that corresponds to a shape memory configuration. Thereafter, the stent can be returned to the collapsed configuration as described herein.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A stent, comprising:
a stent body having a network of struts arranged along a longitudinal axis, a plurality of cells defined between all of the interconnected struts of the network of struts, each of the plurality of cells of the stent body defining convex cells including a cell major axis through spaced apart first and second strut intersection points, each cell major axis is parallel to all other cell major axes and each cell major axis lies in a mirror plane of the cell that symmetrically bisects the cell forming a non-zero cell angle, $\beta$, with respect to the longitudinal axis in the same direction, each of the plurality of cells including at least one strut oriented parallel to the cell major axis.

2. The stent of claim 1, wherein $\beta$ is less than ninety degrees ($0° < \beta < 90°$).

3. The stent of claim 2, wherein $\beta$ is greater than one degree and less than sixty degrees ($1° < \beta < 60°$).

4. The stent of claim 3, wherein $\beta$ is greater than two degrees and less than forty-five degrees ($2° < \beta < 45°$).

5. The stent of claim 4, wherein $\beta$ is greater than five degrees and less than thirty degrees ($5° < \beta < 30°$).

6. The stent of claim 1, wherein the stent body defines a distal end and proximal end, wherein the stent body includes an outer diameter, and wherein the stent is configured so the outer diameter decreases as the distal end and the proximal end are rotated with respect to each other about the longitudinal axis.

7. The stent of claim 1, wherein the stent comprises a shape memory material.

8. The stent of claim 7, wherein the shape memory material comprises a shape memory polymer.

9. The stent of claim 7, wherein the shape memory material comprises a shape memory metal.

10. The stent of claim 9, wherein the shape memory metal comprises a nickel titanium alloy.

11. The stent of claim 1, wherein each of the plurality of cells includes a first strut positioned on a first cell side and a second strut positioned on a second cell side opposite of the first cell side, wherein each of the first and second struts is oriented parallel to the cell major axis.

12. The stent of claim 1, wherein the interconnected struts of the network of struts have a constant width.

13. The stent of claim 1, wherein each of the plurality of cells of the stent body further includes a cell minor axis perpendicular to the cell major axis, the length of the cell along the minor axis providing a minor cell length and the length of the cell along the major axis providing a major cell length greater than the minor cell length.

14. The stent of claim 13, wherein the aspect ratio defined by the ratio of the minor length to the major length is approximately 0.75.

15. The stent of claim 13, wherein the aspect ratio defined by the ratio of the minor length to the major length is approximately 0.50.

16. The stent of claim 13, wherein the aspect ratio defined by the ratio of the minor length to the major length is approximately 0.25.

17. The stent of claim 1, wherein the stent is an open-cell stent.

18. The stent of claim 1, wherein the stent comprises a non-shape memory material.

19. The stent of claim 18, wherein the non-shape memory material comprises any one or any combination of stainless steel, titanium, or a cobalt-chrome alloy.

20. The stent of claim 1, wherein two or more cells are fused together.

21. The stent of claim 1, wherein adjacent convex cells aligned perpendicular to the cell major axis share a common strut oriented parallel to the cell major axis, and adjacent convex cells not aligned perpendicular to the cell major axis share a common strut not parallel to the cell major axis.

22. A self-expanding stent, comprising:
a self-expanding stent body structured to substantially uniformly collapse radially about a longitudinal axis from an expanded configuration to a delivery configuration upon rotation of a proximal end of the stent body with respect to a distal end of the stent body, wherein the stent body includes a plurality of cells defined between interconnected struts of a network of struts arranged along the longitudinal axis, each of the plurality of cells from the proximal end to the distal end of the stent body define convex cells including a major axis that is parallel to all other cell major axes and that lies in a mirror plane of the cell that symmetrically bisects the cell and angled with respect to the longitudinal axis in the same direction to form a non-zero cell angle, $\beta$, each of the plurality of cells including at least one strut oriented parallel to the cell major axis.

23. The stent of claim 22, wherein the stent collapses substantially uniformly.

24. The stent of claim 23, wherein each cell is generally hexagonal.

25. The stent of claim 24, wherein the plurality of cells form a helix around the stent body.

26. The stent of claim 24, wherein two or more cells are fused together.

* * * * *